(12) United States Patent
Jung et al.

(10) Patent No.: US 11,457,898 B2
(45) Date of Patent: Oct. 4, 2022

(54) METHOD OF OBTAINING CONTRAST IMAGE AND ULTRASOUND DIAGNOSIS APPARATUS FOR PERFORMING THE METHOD

(71) Applicant: SAMSUNG MEDISON CO., LTD., Hongcheon-gun (KR)

(72) Inventors: Sung-tae Jung, Seongnam-si (KR); Young-ho Yie, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 963 days.

(21) Appl. No.: 16/026,536

(22) Filed: Jul. 3, 2018

(65) Prior Publication Data

US 2019/0231321 A1 Aug. 1, 2019

(30) Foreign Application Priority Data

Feb. 1, 2018 (KR) ........................ 10-2018-0013086

(51) Int. Cl.
*A61B 8/00* (2006.01)
*A61B 8/08* (2006.01)
*G01S 15/89* (2006.01)

(52) U.S. Cl.
CPC ............... *A61B 8/54* (2013.01); *A61B 8/463* (2013.01); *A61B 8/469* (2013.01); *A61B 8/481* (2013.01); *A61B 8/488* (2013.01); *A61B 8/5246* (2013.01); *G01S 15/8988* (2013.01)

(58) Field of Classification Search
CPC ...................................................... A61B 8/54
See application file for complete search history.

(56) References Cited

U.S. PATENT DOCUMENTS 6,015,384 A * 1/2000 Ramamurthy ........... A61B 8/06
                                                     600/440
6,547,738 B2   4/2003  Lysyansky
6,641,538 B2  11/2003  Nakaya et al.
(Continued)

FOREIGN PATENT DOCUMENTS

JP    2002-360573 A    12/2002
JP    2002-360576 A    12/2002
(Continued)

OTHER PUBLICATIONS

Communication dated Feb. 4, 2019, issued by the European Patent Office in counterpart European Application No. 18186063.3.
(Continued)

*Primary Examiner* — Joseph M Santos Rodriguez
(74) *Attorney, Agent, or Firm* — Sughrue Mion, PLLC

(57) ABSTRACT

Provided are a method of obtaining a contrast image and an ultrasound diagnosis apparatus for performing the method. The ultrasound diagnosis apparatus includes: an ultrasound transceiver; a display; and a controller configured to obtain an ultrasound image and a contrast image of an object by using the ultrasound transceiver, determine a region of interest (ROI) in at least one of the ultrasound image and the contrast image, transmit a flash pulse to destroy a contrast agent in the ROI from among regions of the object, image the contrast agent re-introduced into the ROI, and control the display to display the contrast image of the ROI.

20 Claims, 8 Drawing Sheets

(56) References Cited

U.S. PATENT DOCUMENTS

| | | | |
|---|---|---|---|
| 2003/0105400 A1* | 6/2003 | Yawata | A61B 8/465 600/437 |
| 2004/0092817 A1 | 5/2004 | Brock-Fisher | |
| 2005/0234340 A1 | 10/2005 | Brock-Fisher et al. | |
| 2006/0116583 A1 | 6/2006 | Ogasawara et al. | |
| 2008/0095415 A1 | 4/2008 | Hall | |
| 2008/0097206 A1 | 4/2008 | Chomas et al. | |
| 2008/0242988 A1 | 10/2008 | Yoshida et al. | |
| 2009/0028406 A1* | 1/2009 | Arditi | A61B 8/06 382/131 |
| 2009/0030322 A1 | 1/2009 | Fujiwara et al. | |
| 2011/0230765 A1* | 9/2011 | Guracar | A61B 8/481 600/458 |
| 2016/0302768 A1 | 10/2016 | Miyake | |

FOREIGN PATENT DOCUMENTS

| | | |
|---|---|---|
| JP | 2003-153900 A | 5/2003 |
| JP | 2005-074084 A | 3/2005 |
| JP | 2010-029727 A | 2/2010 |
| JP | 2013-099378 A | 5/2013 |
| JP | 5348920 B2 | 11/2013 |
| KR | 10-2009-0012127 A | 2/2009 |

OTHER PUBLICATIONS

Nico de Jong et al., "Ultrasonic characterization of ultrasound contrast agents", Medical & Biological Engineering & Computing, 47, 8, May 26, 2009, 18 pages total.

* cited by examiner

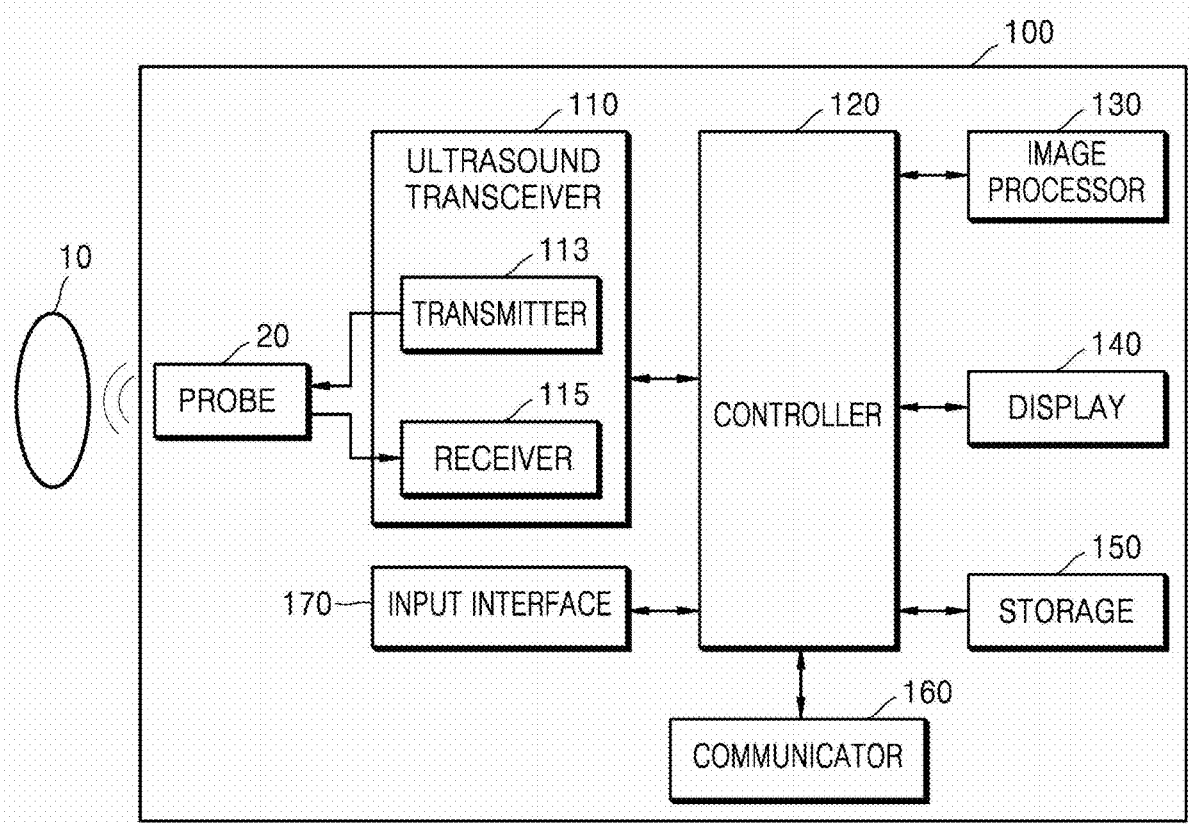

METHOD OF OBTAINING CONTRAST IMAGE AND ULTRASOUND DIAGNOSIS APPARATUS FOR PERFORMING THE METHOD

CROSS-REFERENCE TO RELATED APPLICATION

This application claims the benefit of Korean Patent Application No. 10-2018-0013086, filed on Feb. 1, 2018, in the Korean Intellectual Property Office, the disclosure of which is incorporated herein in its entirety by reference.

BACKGROUND

1. Field

One or more embodiments relate to a method of obtaining a contrast image and an ultrasound diagnosis apparatus for performing the method, and more particularly, to a method of flashing a contrast agent and an ultrasound diagnosis apparatus for performing the method.

2. Description of the Related Art

An ultrasound diagnosis apparatus applies an ultrasound signal generated by a transducer of a probe to an object and receives information of a signal reflected from the object, to obtain at least one image of a body part (e.g., soft tissue or blood flow) inside the object.

The term 'contrast-enhanced ultrasound image' or 'contrast image' may refer to an image obtained by injecting a contrast agent into veins, etc. of an object, transmitting an ultrasound signal to blood vessels of the object, and imaging a reflective signal of the contrast agent that vibrates in the blood vessels.

A contrast agent or a contrast medium that is a chemical substance for increasing a contrast of an image to improve the visibility of tissue or blood vessels during a computer-tomography (CT) scan or a magnetic resonance imaging (MRI) scan may be used to clearly distinguish a biological structure or a lesion from surrounding tissue.

SUMMARY

One or more embodiments include an apparatus and method for reducing destruction of a contrast agent during contrast imaging.

Also, one or more embodiments include an apparatus and method for frequently showing the flow of a contrast agent to a lesion during contrast imaging.

Also, one or more embodiments include an apparatus and method for easily setting a region of interest (ROI) during contrast imaging.

Additional aspects will be set forth in part in the description which follows and, in part, will be apparent from the description, or may be learned by practice of the presented embodiments.

According to one or more embodiments, an ultrasound diagnosis apparatus includes: an ultrasound transceiver; a display; and a controller configured to obtain an ultrasound image and a contrast image of an object by using the ultrasound transceiver, determine a region of interest (ROI) in at least one of the ultrasound image and the contrast image, transmit a flash pulse to destroy a contrast agent in the ROI from among regions of the object, image the contrast agent re-introduced into the ROI, and control the display to display the contrast image of the ROI.

The controller may be further configured to transmit the flash pulse to destroy the contrast agent in the ROI by controlling a probe to transmit the flash pulse from transducer elements corresponding to the ROI from among a plurality of transducer elements of the probe.

The controller may be further configured to transmit the flash pulse to destroy the contrast agent in the ROI by determining the ROI as a focusing region and performing beamforming based on the determined focusing region.

The controller may be further configured to receive a user input that adjusts a mechanical index of the flash pulse and transmit the flash pulse having the adjusted mechanical index.

The controller may be further configured to control the display to display an image indicating the ROI in the ultrasound image at a position of the ROI in the contrast image.

The ultrasound diagnosis apparatus may further include a user input interface configured to receive a user input for setting the ROI in the at least one of the ultrasound image and the contrast image of the object.

The controller may be further configured to, when a user input that measures a certain region in the ultrasound image is received, determine the measured certain region as the ROI.

The ultrasound image may be a color Doppler image, and the controller may be further configured to determine a region where a color Doppler flow in the color Doppler image is displayed as the ROI.

The controller may be further configured to control the display to display the ultrasound image and the contrast image together and display a position of a region in the ultrasound image corresponding to the ROI set in the contrast image, on the ultrasound image.

The controller may be further configured to, when the ROI is determined, display an expected contrast image to be obtained when the flash pulse is transmitted to the determined ROI.

BRIEF DESCRIPTION OF THE DRAWINGS

These and/or other aspects will become apparent and more readily appreciated from the following description of the embodiments, taken in conjunction with the accompanying drawings in which reference numerals denote structural elements and in which:

FIG. 8 is a block diagram illustrating a configuration of the ultrasound diagnosis apparatus, according to an embodiment.

DETAILED DESCRIPTION

Figure 1:
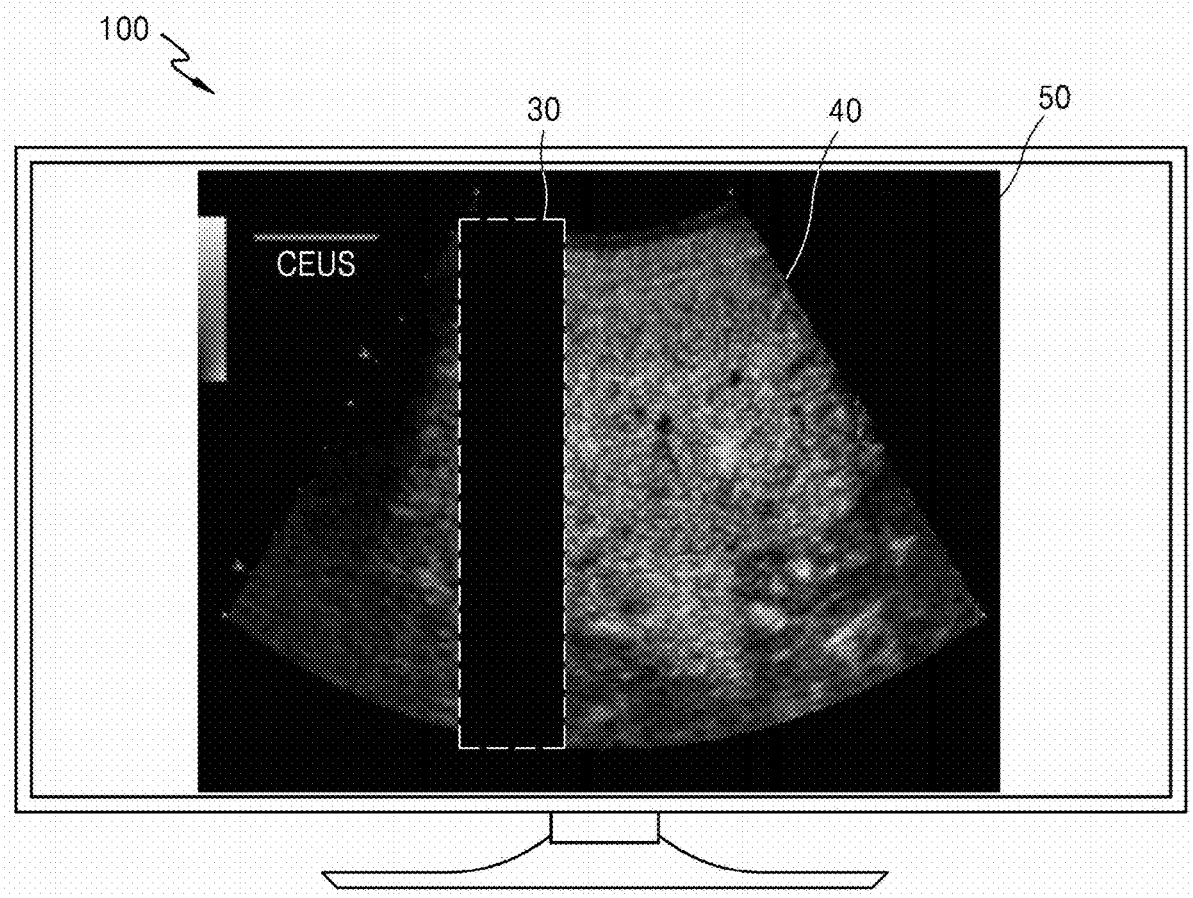
FIG. 1 is a view for explaining a method by which an ultrasound diagnosis apparatus removes only a contrast agent of a certain region in a scan region during contrast imaging, according to an embodiment.

Hereinafter, principles and embodiments of the present disclosure will be described in detail in order to fully convey the scope of the present disclosure and enable one of ordinary skill in the art to embody and practice the present disclosure. The embodiments may be implemented in various forms.

The same reference numerals denote the same elements throughout the specification. All elements of embodiments are not described in the specification, and descriptions of matters well known in the art to which the present disclosure pertains or repeated descriptions between embodiments will not be given. Terms such as 'part' and 'portion' used herein denote those that may be embodied by software or hardware. According to embodiments, a plurality of parts or portions may be embodied by a single unit or element, or a single part or portion may include a plurality of elements. Operation principles and embodiments of the present disclosure will now be explained with reference to the accompanying drawings.

In embodiments, an image may include any medical image acquired by a medical imaging apparatus such as an ultrasound imaging apparatus.

Also, in the present specification, an 'object', which is a thing to be imaged, may include a human, an animal, or a part thereof. For example, an object may include a part of a human (e.g., an organ) or a phantom.

Throughout the specification, an "ultrasound image" refers to an image of an object processed based on an ultrasound signal transmitted to the object and reflected therefrom.

As used herein, the term "and/or" includes any and all combinations of one or more of the associated listed items. Expressions such as "at least one of", when preceding a list of elements, modify the entire list of elements and do not modify the individual elements of the list.

The present disclosure will now be described more fully with reference to the accompanying drawings, in which embodiments of the present disclosure are shown.

FIG. 1 is a view for explaining a method by which an ultrasound diagnosis apparatus 100 removes only a contrast agent of a certain region in a scan region during contrast imaging, according to an embodiment.

As a contrast agent flows through blood vessels, a contrast image may show a flow of the contrast agent, and the flow of the contrast agent may reveal a location, a shape, or characteristics of a lesion. For example, since tumor tissue includes more blood vessels than surrounding tissue, a larger amount of contrast agent may be introduced into the tumor tissue, thereby making the tumor tissue brighter than the surrounding tissue.

However, since a contrast agent has characteristics similar to those of air bubbles or is discharged from the body, the amount of contrast agent passing through organs and remaining in the body may gradually decrease as time passes. For example, when a contrast agent is not artificially destroyed, the contrast agent may remain in the body for about 5 minutes.

When a contrast agent is introduced into a scan region and is fully filled in blood vessels in the scan region, a user may monitor again a flow of the contrast agent introduced into the scan region by flashing the contrast agent in the scan region. Also, as the amount of contrast agent remaining in the body is reduced, in order to rapidly destroy the contrast agent in the body in a short time for the purpose of re-injection of the contrast agent, the user may remove the contrast agent remaining in the body in a short time by flashing the contrast agent in the scan region several times.

The term 'flashing' may refer to transmitting an ultrasound pulse with a mechanical index (MI) great enough to destroy the contrast agent into the body. For example, the ultrasound diagnosis apparatus 100 may destroy the contrast agent in the scan region by transmitting an ultrasound pulse with an MI of 1.8 to the scan region. The term 'MI' may refer to a peak negative pressure of an ultrasound signal. Also, the ultrasound pulse for destroying the contrast agent may be referred to as a flash pulse. The contrast agent may be more easily destroyed by a flash pulse with a greater MI. In contrast, the contrast agent may not be destroyed by a flash pulse with an MI equal to or less than a reference value.

A region of interest (ROI) of the user may be a certain region in the scan region, instead of the entire scan region. Also, according to cases, the user may want to see a flow of the contrast agent introduced into the entire scan region or may want to see a flow of the contrast agent introduced into a certain ROI of the scan region.

However, if the entire scan region is continuously flashed, the amount of contrast agent that is destroyed may increase. As the amount of contrast agent that is destroyed increases, a cycle in which the contrast agent is re-injected may decrease. Also, if the entire scan region is flashed, a time taken for the contrast agent to be introduced into the ROI after flashing may increase, thereby increasing a contrast imaging time.

Referring to FIG. 1, the ultrasound diagnosis apparatus 100 may remove only a contrast agent of a certain region of a scan region 40 during contrast imaging.

For example, as a user input that sets an ROI 30 on a contrast image 50 is received and a user input that presses a flash button is received, the ultrasound diagnosis apparatus 100 may flash only the contrast agent in the ROI 30 of the entire scan region 40.

Since only the contrast agent in the ROI 30 of the entire scan region 40 is flashed, the amount of contrast agent that is destroyed in the body may be reduced and a cycle in which the contrast agent is re-introduced into the ROI 30 may also be reduced.

Figure 2:
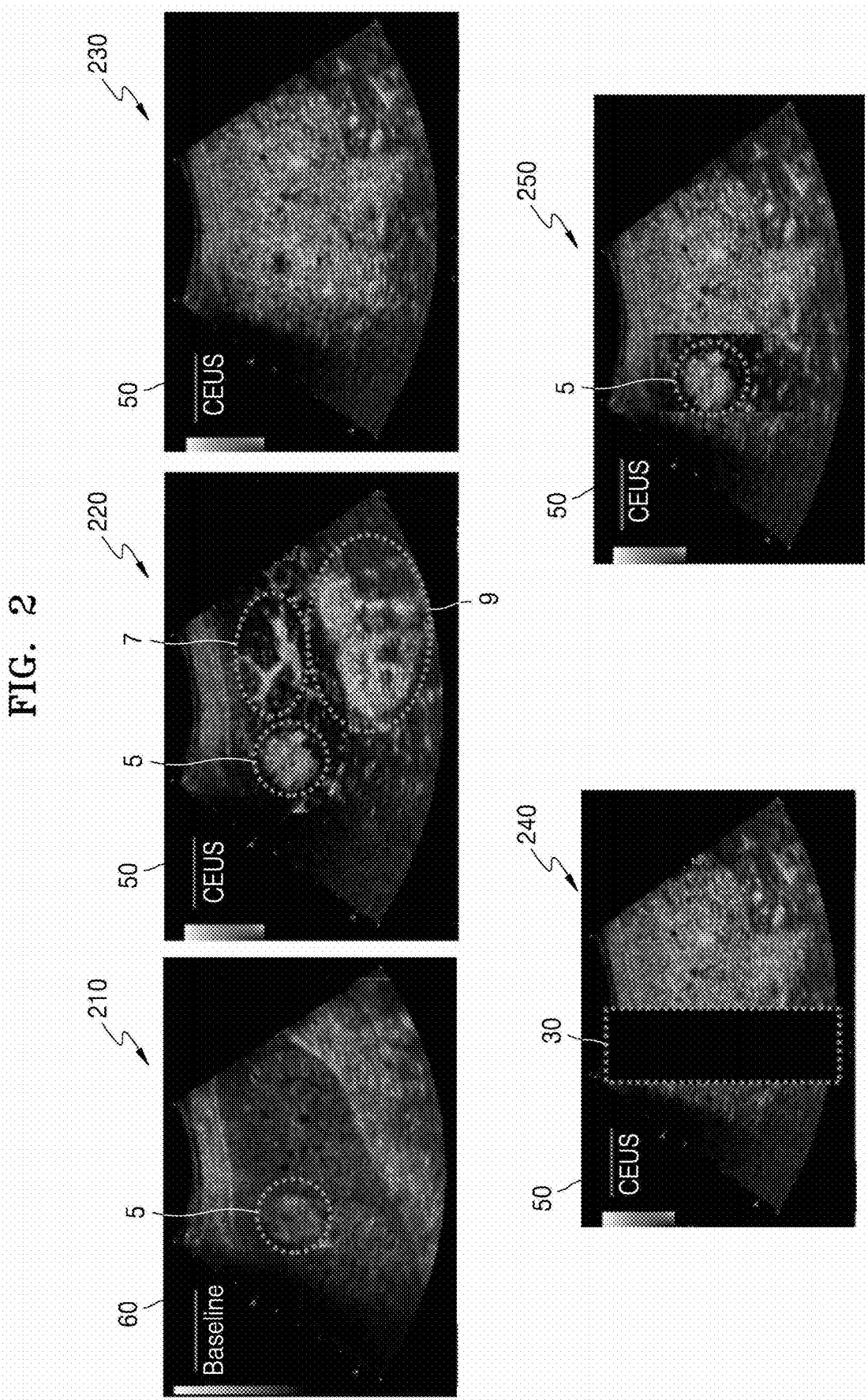
FIG. 2 is a view for explaining a method by which the ultrasound diagnosis apparatus displays a contrast image of a region of interest (ROI) by flashing only a contrast agent of the ROI of a scan region, according to an embodiment.

FIG. 2 is a view for explaining a method by which the ultrasound diagnosis apparatus 100 displays a contrast image of the ROI 30 by flashing only a contrast agent of the ROI 30 of a scan region, according to an embodiment.

Referring to an image denoted by reference numeral 210, a user may check a region of a lesion 5 to be scanned based on a B-mode image 60 before contrast imaging.

For example, as a user input for obtaining the B-mode image 60 is received, the ultrasound diagnosis apparatus 100 may transmit an ultrasound signal for B-mode imaging to an object and may generate and display the B-mode image 60 based on an echo signal received from the object.

Referring to an image denoted by reference numeral 220, as a user input for obtaining the contrast image 50 is received, the ultrasound diagnosis apparatus 100 may transmit an ultrasound signal for contrast imaging to the object and may generate and display the contrast image 50 based on an echo signal received from the object.

In this case, the user may inject a contrast agent into the object before B-mode imaging, and may inject the contrast agent into the object before contrast imaging after the B-mode imaging. Also, the user may start the contrast imaging at the same position as a position of a probe during the B-mode imaging, without changing the position of the probe after the B-mode imaging.

As the contrast agent is introduced into the scan region, the contrast agent may be first introduced into an organ 9, a thick blood vessel 7, or a tumor 5 having thick blood vessels and a high density. Accordingly, in the obtained contrast image 50, the lesion 5, the thick blood vessel 7, and the organ 9 in the scan region may look brighter than other regions.

Also, the user may determine a type of the tumor 5 based on a speed or characteristics of the contrast agent that is introduced. For example, the user may determine a type of the tumor 5 based on whether a brightness level gradually increases from the inside of the tumor 5 to the outside of the tumor 5 or gradually increases from the outside of the tumor 5 to the inside of the tumor 5.

Referring to an image denoted by reference numeral 230, as the contrast agent is introduced into even small blood vessels in the scan region, the entire scan region in the contrast image 50 brightens, thereby causing the user to fail to distinguish the tumor 5.

Referring to an image denoted by reference numeral 240, the ultrasound diagnosis apparatus 100 may flash only the contrast agent in the ROI 30 of the scan region. The ROI 30 may be set by the user, or may be automatically determined by the ultrasound diagnosis apparatus 100 according to the user's manipulation of the B-mode image 60. In the image denoted by reference numeral 240, the ROI 30 may be a region where the tumor 5 is located.

As only the contrast agent in the ROI 30 is flashed, the ROI 30 on the contrast image may be in black and white and regions other than the ROI 30 may be bright.

Referring to an image denoted by reference numeral 250, as the contrast agent is re-introduced into the ROI 30 from the regions other than the ROI 30, the contrast image 50 may show again a flow of the contrast agent introduced into the tumor 5.

Figure 3:
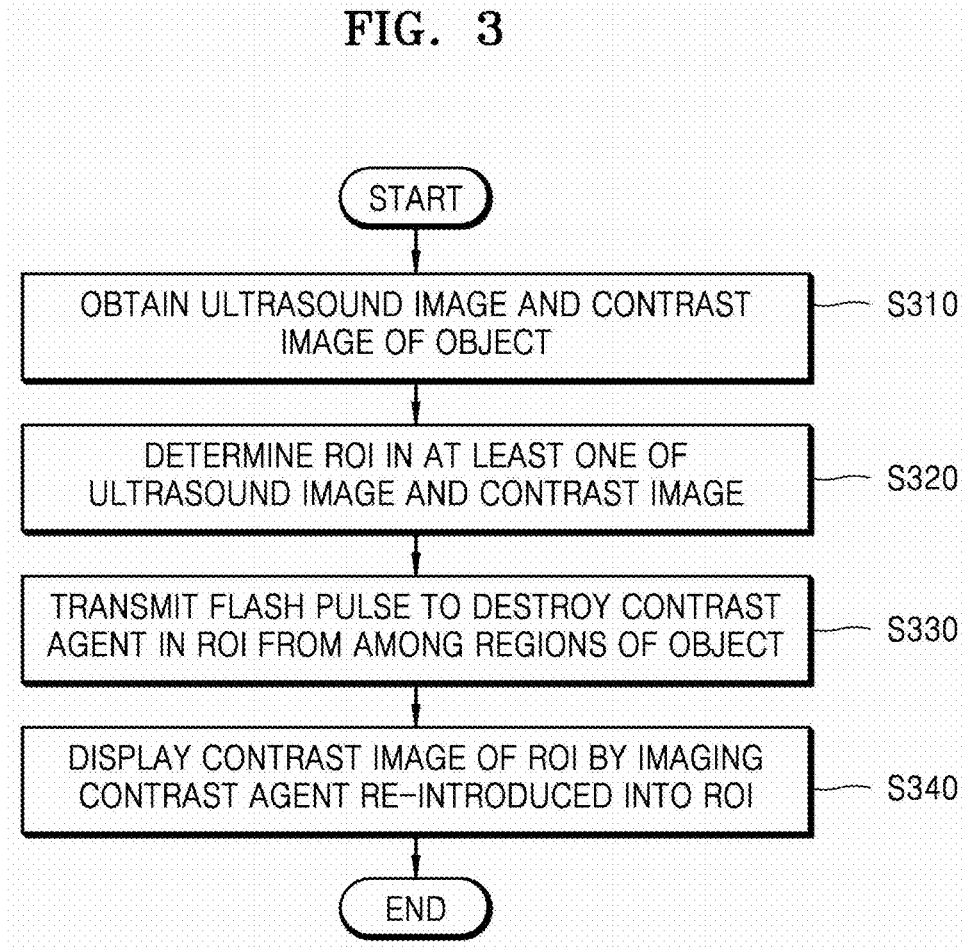
FIG. 3 is a flowchart of a method by which the ultrasound diagnosis apparatus flashes a contrast agent located in an ROI of a scan region, according to an embodiment.

FIG. 3 is a flowchart of a method by which the ultrasound diagnosis apparatus 100 flashes a contrast agent located in an ROI of a scan region, according to an embodiment.

In operation S310, the ultrasound diagnosis apparatus 100 may obtain an ultrasound image of an object and a contrast image of the object. Examples of the ultrasound image may include a B-mode image, an M-mode image, and a Doppler image. The ultrasound image and the contrast image may be two-dimensional (2D) images or three-dimensional (3D) images.

The ultrasound diagnosis apparatus 100 may include a menu or a button for obtaining the ultrasound image and the contrast image. As a user input for obtaining the ultrasound image of the object is received, the ultrasound diagnosis apparatus 100 may obtain the ultrasound image of a scan region by transmitting a first ultrasound signal to the object and receiving an ultrasound echo signal from the object. Also, as a user input for obtaining the contrast image of the object after a contrast agent is injected is received, the ultrasound diagnosis apparatus 100 may obtain the contrast image of the scan region by transmitting a second ultrasound signal to the object and receiving an ultrasound echo signal reflected from the contrast agent in the object. The first ultrasound signal and the second ultrasound signal may be different from each other.

In this case, the ultrasound diagnosis apparatus 100 may display the ultrasound image and the contrast image together. Also, according to embodiments, when a toggle mode is provided, the ultrasound diagnosis apparatus 10 may alternately display the ultrasound image and the contrast image based on a user input that selects a toggle button. Also, according to embodiments, the ultrasound diagnosis apparatus 100 may display the ultrasound image and the contrast image so that the ultrasound image and the contrast image overlap each other.

In operation S320, the ultrasound diagnosis apparatus 100 may determine an ROI in at least one of the ultrasound image and the contrast image.

The ultrasound diagnosis apparatus 100 may receive a user input that sets the ROI in at least one of the ultrasound image and the contrast image. For example, the ultrasound diagnosis apparatus 100 may provide a menu for setting a region to be flashed to at least one of the ultrasound image and the contrast image.

The ultrasound diagnosis apparatus 100 may receive a user input that sets the ROI on the ultrasound image, or may receive a user input that sets the ROI on the contrast image.

Also, as a user input that measures a certain region in the ultrasound image is received, the ultrasound diagnosis apparatus 100 may automatically determine the measured certain region as the ROI. Also, the ultrasound diagnosis apparatus 100 may provide guide information for checking whether the measured certain region is to be set as the ROI and may determine the measured certain region as the ROI based on a user response.

Also, as a user input that enlarges a certain region in the ultrasound image is received, the ultrasound diagnosis apparatus 100 may determine the enlarged certain region as the ROI. Also, the ultrasound diagnosis apparatus 100 may provide guide information for checking whether the enlarged certain region is to be set as the ROI and may determine the enlarged certain region as the ROI based on a user response.

Also, when the ultrasound image is a color Doppler image, the ultrasound diagnosis apparatus 100 may automatically determine a region where a color Doppler flow in the color Doppler image is displayed as the ROI. Also, when the ultrasound image is a color Doppler image, the ultrasound diagnosis apparatus 100 may automatically determine a region set by the user in the color Doppler image as the ROI. Once the ultrasound diagnosis apparatus 100 automatically determines the ROI, the ultrasound diagnosis apparatus 100 may display the determined ROI so that the user may check the ROI.

The ROI may have, but is not limited to, a box shape, a circular shape, or a scan line shape.

Also, a plurality of the ROIs may be provided. For example, the number of ROIs may be 2, 3, 4, or more.

In operation S330, the ultrasound diagnosis apparatus 100 may transmit a flash pulse to destroy the contrast agent in the ROI from among regions of the object.

The ultrasound diagnosis apparatus 100 may receive a user input for transmitting the flash pulse to the object. The ultrasound diagnosis apparatus 100 may include a menu or a button for transmitting the flash pulse to the object.

As a user input for transmitting the flash pulse is received, the ultrasound diagnosis apparatus 100 may transmit the flash pulse to destroy the contrast agent in the ROI by controlling a probe to transmit the flash pulse from transducer elements corresponding to the ROI from among all transducer elements of the probe. The transducer elements may be referred to as elements or probe elements according to embodiments.

Also, the ultrasound diagnosis apparatus 100 may transmit the flash pulse to destroy the contrast agent in the ROI by determining the ROI as a focusing region and performing beamforming based on the focusing region.

Also, the ultrasound diagnosis apparatus 100 may transmit the flash pulse to the same ROI two or more times. For example, as a user input for destroying the contrast agent in the ROI is received, the ultrasound diagnosis apparatus 100 may transmit the flash pulse to the same ROI a preset number of times. The number of times the flash pulse is transmitted may be determined by a user input.

When the ROI is located slightly far from the transducer elements, the contrast agent located in a region through which the flash pulse transmitted from the transducer elements passes before reaching the ROI or a region through which the flash pulse is passes after reaching the ROI may also be destroyed. Also, even when the ROI has a scan line shape, since a beam generated when the flash pulse is beamformed and is transmitted to the ROI is not linear, the contrast agent located in a surrounding region outside the ROI may also be destroyed. Accordingly, even when the ultrasound diagnosis apparatus 100 transmits the flash pulse to destroy the contrast agent in the ROI from among the regions of the object, the contrast agent located in the surrounding region outside the ROI may also be destroyed. However, since a total size of the ROI and the surrounding region outside the ROI is much less than a size of the entire scan region, the amount of contrast agent that is destroyed may be reduced.

Also, as the ROI is determined, the ultrasound diagnosis apparatus 100 may display an expected contrast image to be obtained when the flash pulse is transmitted to the determined ROI. For example, the ultrasound diagnosis apparatus 100 may extract frame data displayed on the ROI of the contrast image based on the contrast image obtained in operation S310, may generate a video corresponding to the ROI based on the extracted frame data, and may display the generated video on the ROI of the expected contrast image.

Also, although most users may want to destroy the whole contrast agent in the ROI by setting an MI to be equal to or greater than a reference value, some users may want to reduce the amount of contrast agent that is destroyed and a cycle in which the contrast agent is filled again by destroying only a part of the contrast agent in the ROI.

The ultrasound diagnosis apparatus 100 may provide a user interface for adjusting an MI of the flash pulse. The ultrasound diagnosis apparatus 100 may receive a user input that adjusts the MI of the flash pulse through the user interface and may transmit the flash pulse having the adjusted MI to the object.

Also, as a user input that adjusts the MI of the flash pulse is received, the ultrasound diagnosis apparatus 100 may display the expected contrast image to be obtained when the flash pulse having the adjusted MI is transmitted. In operation S340, the ultrasound diagnosis apparatus 100 may display the contrast image of the ROI by imaging the contrast agent re-introduced into the ROI.

As a user input for imaging the contrast image is received, the ultrasound diagnosis apparatus 100 may generate the contrast image of the scan region by transmitting a second ultrasound signal to the object and receiving an ultrasound echo signal from the contrast agent in the object.

As the contrast agent located outside the ROI is introduced into the ROI, the contrast image may show a flow of the contrast agent introduced into the ROI.

Figure 4:
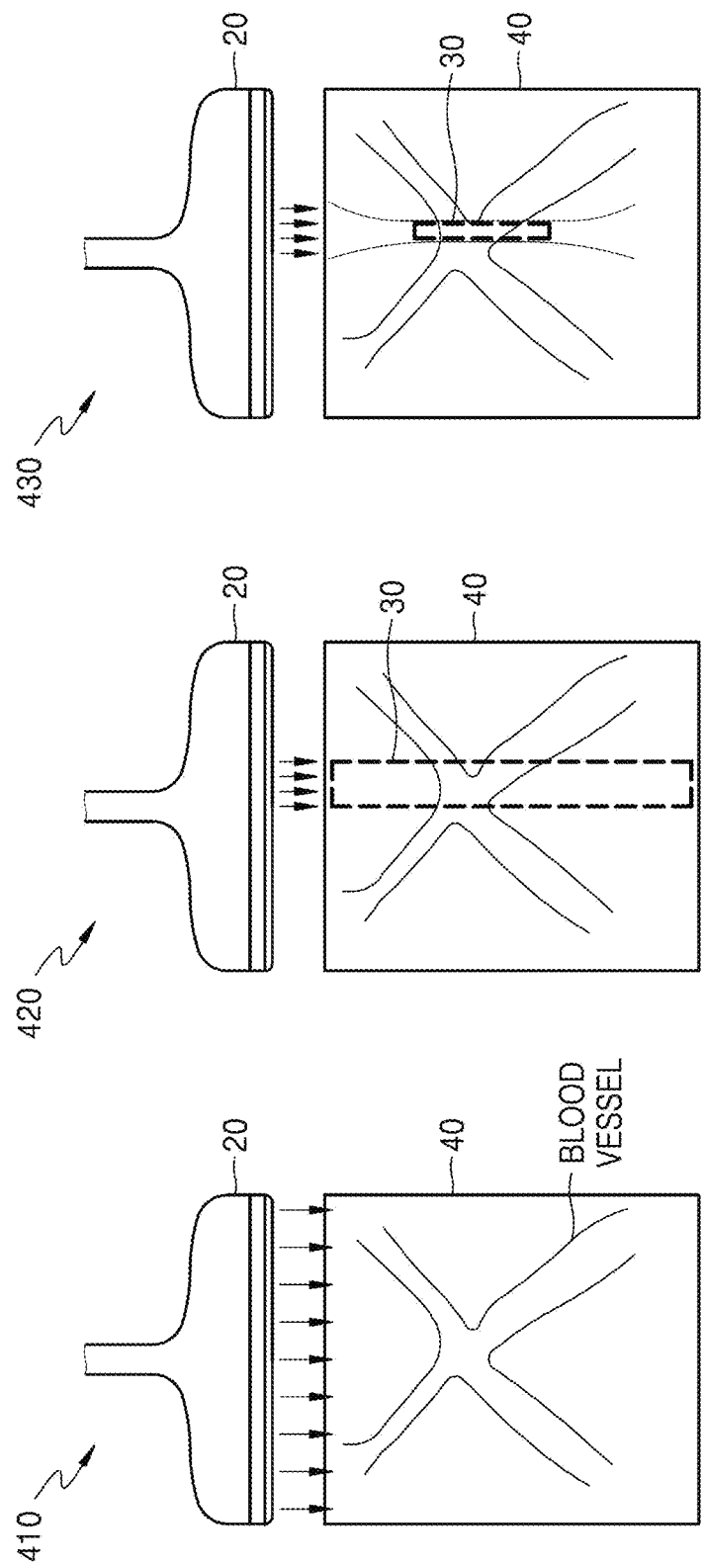
FIG. 4 is a view for explaining a method by which the ultrasound diagnosis apparatus transmits a flash pulse to destroy only a contrast agent located in an ROI of a scan region, according to an embodiment.

FIG. 4 is a view for explaining a method by which the ultrasound diagnosis apparatus 100 transmits a flash pulse to destroy only a contrast agent located in an ROI of a scan region, according to an embodiment.

Referring to an image denoted by reference numeral 410 of FIG. 4, the ultrasound diagnosis apparatus 100 may destroy a contrast agent located in the entire scan region 40 by transmitting a flash pulse to the entire scan region 40. For example, the ultrasound diagnosis apparatus 100 may control a probe 20 to transmit the flash pulse to the entire scan region 40 from all transducer elements located in the probe 20.

Referring to an image denoted by reference numeral 420 of FIG. 4, the ultrasound diagnosis apparatus 100 may transmit the flash pulse to destroy only the contrast agent located in the ROI 30 of the scan region 40.

The ultrasound diagnosis apparatus 100 may transmit the flash pulse to destroy the contrast agent in the ROI 30 by controlling a transceiver to transmit the flash pulse only from transducer elements corresponding to the ROI 30 from among a plurality of transducer elements of the probe 20.

For example, the ultrasound diagnosis apparatus 100 may determine transducer elements located within a pre-determined distance from a transducer element that is the closest to the ROI 30 from among the plurality of transducer elements as the transducer elements corresponding to the ROI 30, based on a position of the ROI 30.

Also, for example, the ultrasound diagnosis apparatus 100 may determine scan lines over which the ROI 30 extends from among a plurality of scan lines constituting an ultrasound image or a contrast image, and may determine transducer elements located within a pre-determined distance from the determined scan lines as the transducer elements corresponding to the ROI 30.

Referring to an image denoted by reference numeral 430 of FIG. 4, the ultrasound diagnosis apparatus 100 may transmit the flash pulse to destroy the contrast agent in the ROI 30 by determining the ROI 30 as a focusing region and performing beamforming based on the focusing region.

Also, when a plurality of the ROIs 30 are provided, the ultrasound diagnosis apparatus 100 may destroy the contrast agent in the plurality of ROIs by determining transducer elements respectively corresponding to the plurality of ROIs 30 and controlling the transceiver to transmit the flash pulse only from the determined transducer elements.

Figure 5:
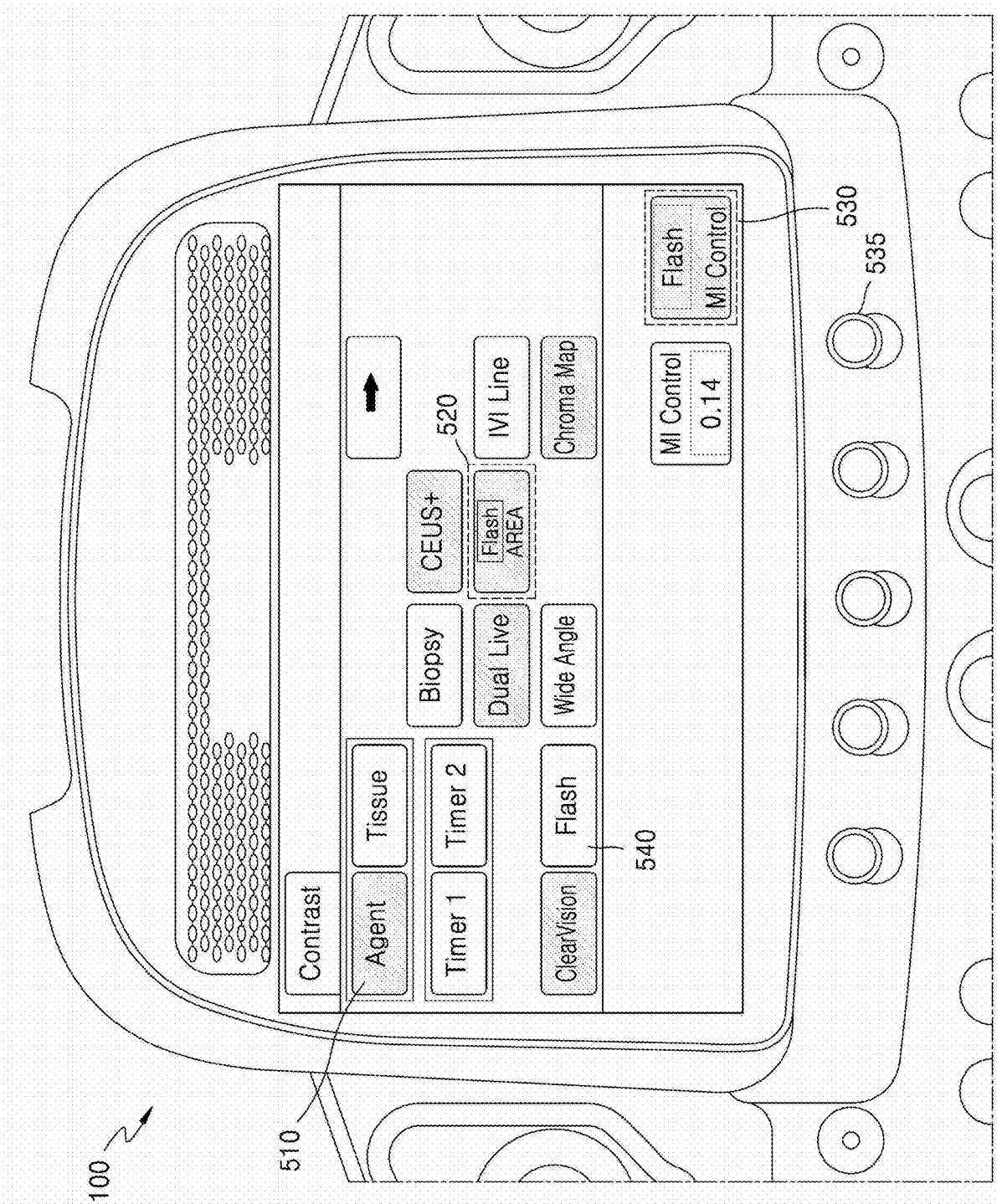
FIG. 5 is a view illustrating a user interface through which the ultrasound diagnosis apparatus obtains a contrast image, according to an embodiment.

FIG. 5 is a view illustrating a user interface through which the ultrasound diagnosis apparatus 100 obtains a contrast image, according to an embodiment.

Referring to FIG. 5, the ultrasound diagnosis apparatus 100 may provide a user interface for obtaining a contrast image.

The ultrasound diagnosis apparatus 100 may display a contrast imaging button 510 for obtaining the contrast image.

As a user input that selects the contrast imaging button 510 is received, the ultrasound diagnosis apparatus 100 may transmit a second ultrasound signal for obtaining the contrast image by using a probe to a scan region, may receive an echo signal reflected from a contrast agent in the scan region, and display the contrast image of the scan region.

Figure 6:
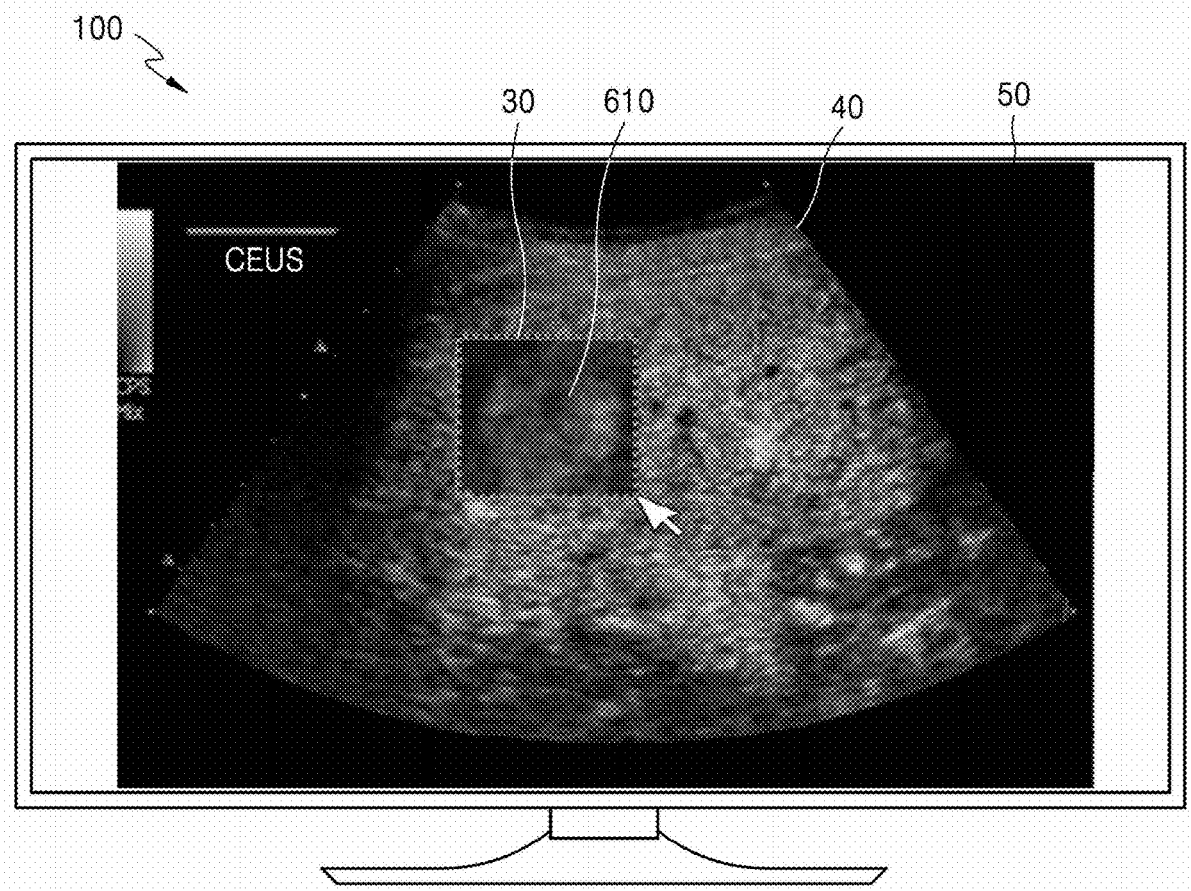
FIG. 6 is a view for explaining a method by which the ultrasound diagnosis apparatus displays data of an ultrasound image corresponding to an ROI on a contrast image, according to an embodiment.

Also, the ultrasound diagnosis apparatus 100 may display an ROI setting button 520 for setting an ROI to be flashed. As a user input that selects the ROI setting button 520 is received, the ultrasound diagnosis apparatus 100 may provide a user interface for setting the ROI on the contrast image or an ultrasound image. For example, as shown in FIG. 6, as a user input that selects a start point and an end point by using a cursor is received, the ultrasound diagnosis apparatus 100 may provide a user interface that selects a box region with the selected start point and the selected end point as vertices as the ROI.

Figure 7:
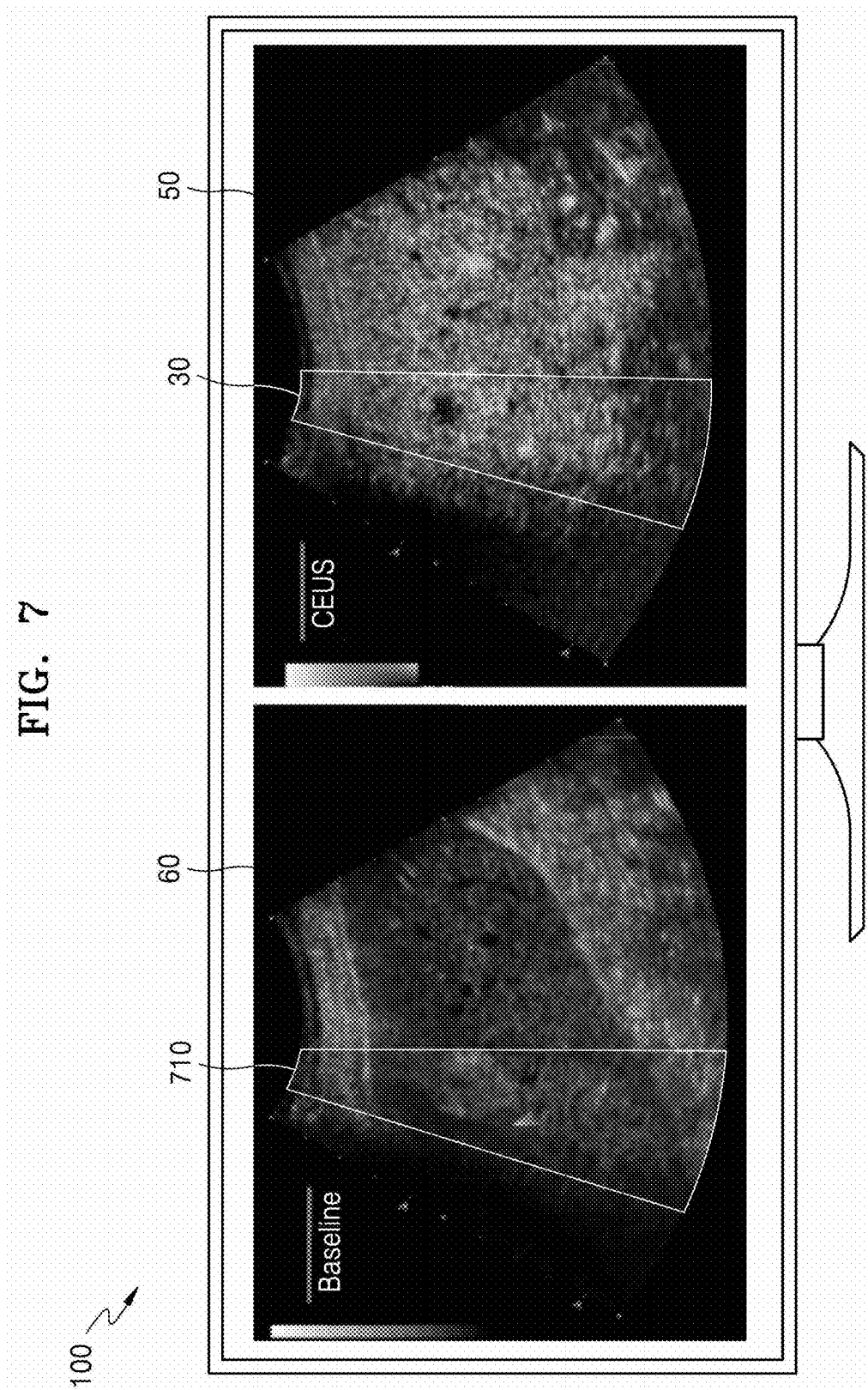
FIG. 7 is a view for explaining a method by which the ultrasound diagnosis apparatus displays a position of a region in an ultrasound image corresponding to an ROI set on a contrast image, according to an embodiment.

Also, according to an embodiment, as shown in FIG. 7, as a user input that selects a start line and an end line is received, a user interface that selects a scan line from the start line to the end line as the ROI may be provided.

Also, according to embodiments, a user interface that may allow the ROI to be drawn with a pen or a brush may be provided.

Also, the ultrasound diagnosis apparatus 100 may display an MI adjusting button 530 for adjusting an MI of a flash pulse.

As a user input that selects the MI adjusting button 530 and turns a knob 535 corresponding to the MI adjusting button 530 is received, an MI value of the flash pulse selected by a user may be identified.

Also, the ultrasound diagnosis apparatus 100 may display a flash button 540 for transmitting the flash pulse in the determined ROI. As a user input that selects the flash button 540 is received, the ultrasound diagnosis apparatus 100 may transmit the flash pulse having the identified MI value in the ROI.

FIG. 6 is a view for explaining a method by which the ultrasound diagnosis apparatus 100 displays data of an ultrasound image corresponding to an ROI on a contrast image, according to an embodiment.

Referring to FIG. 6, the ultrasound diagnosis apparatus 100 may receive a user input that sets the ROI 30 on the contrast image 50. As a user input that selects a start point and an end point by using a cursor is received, the ultrasound diagnosis apparatus 100 may determine a box region with the selected start point and the selected end point as vertices as the ROI 30.

When a user sets the ROI 30 on the contrast image 50, a contrast agent may be filled even in small blood vessels in a scan region and thus it may be difficult to determine a location of a lesion on the contrast image 50. Accordingly, the user may be difficult to determine whether the ROI 30 includes a lesion.

The ultrasound diagnosis apparatus 100 may determine data of the ultrasound image corresponding to the ROI 30 and may display an image 610 indicating the determined data on the ROI 30 in the contrast image 50.

Since ultrasound imaging is performed and then contrast imaging is performed in a state where a probe is fixed, a position of the probe when the ultrasound image is obtained and a position of the probe when the contrast image 50 is obtained may be the same. Accordingly, the data of the ultrasound image corresponding to the ROI 30 may be data in a region of the ultrasound image whose position is the same as a position of the ROI 30.

Since the ultrasound diagnosis apparatus 100 displays the image 610 indicating the data of the ultrasound image corresponding to the ROI 30 on the ROI 30 in the contrast image 50, the user may determine whether the selected ROI 30 includes a lesion.

FIG. 7 is a view for explaining a method by which the ultrasound diagnosis apparatus 100 displays a position of a region 710 in an ultrasound image, e.g., the B-mode image 60, corresponding to the ROI 30 set on the contrast image 50, according to an embodiment.

Referring to FIG. 7, the ultrasound diagnosis apparatus 100 may receive a user input that selects the ROI 30 on the contrast image 50. For example, as a user input that selects a start line and an end line on the contrast image 50 is received, the ultrasound diagnosis apparatus 100 may determine a scan line from the start line to the end line as the ROI 30.

As the ROI 30 on the contrast image 50 is determined, the ultrasound diagnosis apparatus 100 may display a position of the region 710 in the ultrasound image corresponding to the ROI 30 on the ultrasound image.

FIG. 8 is a block diagram illustrating a configuration of the ultrasound diagnosis apparatus 100, i.e., a diagnostic apparatus, according to an embodiment.

Referring to FIG. 8, the ultrasound diagnosis apparatus 100 may include the probe 20, an ultrasound transceiver 110, a controller 120, an image processor 130, one or more displays 140, a storage 150, a communicator 160, and an input interface 170.

The ultrasound diagnosis apparatus 100 may be of a cart-type or a portable-type ultrasound diagnosis apparatus that is portable, moveable, mobile, or hand-held. Examples of the portable-type ultrasound diagnosis apparatus 100 may include a smart phone, a laptop computer, a personal digital assistant (PDA), and a tablet personal computer (PC), each of which may include a probe and a software application, but embodiments are not limited thereto.

The probe 20 may include a plurality of transducer elements. The plurality of transducer elements may transmit ultrasound signals to an object 10 in response to transmitting signals received by the probe 20, from a transmitter 113. The plurality of transducer elements may receive ultrasound signals reflected from the object 10 to generate reception signals. In addition, the probe 20 and the ultrasound diagnosis apparatus 100 may be formed in one body, or the probe 20 and the ultrasound diagnosis apparatus 100 may be formed separately but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to the plurality of transducer elements based on a position and a focal point of the plurality of transducer elements included in the probe 20.

The controller 120 may control an ultrasound receiver 115 to generate ultrasound data by converting reception signals received from the probe 20 from analogue to digital signals and summing the reception signals converted into digital form, based on a position and a focal point of the plurality of transducer elements.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include one or more displays 140 according to the present embodiment. The display 140 may include a touch screen in combination with a touch panel.

The controller 120 may control the operations of the ultrasound diagnosis apparatus 100 and the flow of signals between the internal elements of the ultrasound diagnosis apparatus 100. The controller 120 may include a memory for storing a program or data to perform functions of the ultrasound diagnosis apparatus 100 and a processor for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but embodiments are not limited thereto.

The controller 120 may obtain an ultrasound image and a contrast image of an object by using the ultrasound transceiver 110.

Also, the controller 120 may determine an ROI in at least one of the ultrasound image and the contrast image.

Also, the controller 120 may transmit a flash pulse to destroy a contrast agent in the ROI from among regions of the object.

For example, the controller 120 may transmit the flash pulse to destroy the contrast agent in the ROI by controlling the probe 20 to transmit the flash pulse only from transducer elements corresponding to the ROI from among a plurality of transducer elements of the probe 20.

Also, for example, the controller 120 may transmit the flash pulse to destroy the contrast agent in the ROI by determining the ROI as a focusing region and performing beamforming based on the determined focusing region.

Also, the controller 120 may control the display 140 to display the contrast image of the ROI by imaging the contrast agent re-introduced into the ROI.

For example, the controller 120 may transmit a second ultrasound signal for contrast imaging to the object and may obtain the contrast image of the ROI based on an ultrasound echo signal reflected from the contrast agent in the object. Also, the controller 120 may control the display 140 to display the obtained contrast image.

Also, the controller 120 may receive a user input that adjusts an MI of the flash pulse through the input interface 170 such as a knob.

Also, the controller 120 may transmit the flash pulse having the adjusted MI.

Also, the controller 120 may control the display 140 to display an image indicating the ROI in the ultrasound image at a position of the ROI in the contrast image.

Also, the controller 120 may control the input interface 170 to receive a user input that sets the ROI in at least one of the ultrasound image and the contrast image of the object.

Also, as a user input that measures a certain region in the ultrasound image is received, the controller 120 may determine the measured certain region as the ROI.

Also, the controller 120 may determine a region where a color Doppler flow in a color Doppler image is displayed as the ROI.

Also, the controller 120 may control the display the display 140 to display the ultrasound image and the contrast image together and display a position of a region in the ultrasound image corresponding to the ROI set in the contrast image, on the ultrasound image.

Also, as the ROI is determined, the controller 120 may generate an expected contrast image to be obtained when the flash pulse is transmitted to the determined ROI.

Also, the controller 120 may control the display 140 to display the generated expected contrast image.

The present disclosure may be embodied as a recording medium including instructions that may be executed in computers, e.g., a program module executed in computers. A computer-readable recording medium may be an arbitrary available medium accessible by a computer, and examples thereof include all volatile and non-volatile media and separable and non-separable media. Further, examples of the computer-readable recording medium may include a computer storage medium and a communication medium. Examples of the computer storage medium include all volatile and non-volatile media and separable and non-separable media, which have been implemented by an arbitrary method or technology, for storing information such as computer-readable commands, data structures, program modules, and other data. The communication medium typically includes a computer-readable command, a data structure, a program module, other data of a modulated data signal, or another transmission mechanism, and an example thereof includes an arbitrary information transmission medium.

Also, the term "unit" used herein may be a hardware component such as a processor a circuit and/or a software component executed in a hardware component such as a processor.

While the present disclosure has been particularly shown and described with reference to embodiments thereof, it will be understood by one of ordinary skill in the art that various changes in form and details may be made therein without departing from the spirit and scope of the present disclosure as defined by the following claims. Hence, it will be understood that the embodiments described above are not limiting of the scope of the present disclosure. For example, each component described in a single type may be executed in a distributed manner, and components described distributed may also be executed in an integrated form.

The scope of the present disclosure is indicated by the claims rather than by the detailed description of the present disclosure, and it should be understood that the claims and all modifications or modified forms drawn from the concept of the claims are included in the scope of the present disclosure.

What is claimed is:

1. An ultrasound diagnosis apparatus comprising:
   an ultrasound transceiver;
   a display; and
   a controller configured to:
   obtain an ultrasound image and a contrast image of a scan region of an object by using the ultrasound transceiver, wherein the contrast image is an image showing a signal reflected by an injected contrast agent;
   determine a region of interest (ROI) in at least one image of the ultrasound image and the contrast image, wherein the contrast agent includes a first contrast agent in the ROI and a second contrast agent in an area other than the ROI;
   transmit a flash pulse to destroy the first contrast agent;
   image the second contrast agent re-introduced into the ROI; and
   control the display to display a flow image of the second contrast agent that has been re-introduced into the ROI,
   wherein when a tumor is in the ROI, the flow image shows a flow of the second contrast agent flowing into the tumor as the second contrast agent is re-introduced into the ROI.

2. The ultrasound diagnosis apparatus of claim 1, wherein the controller is further configured to transmit the flash pulse to destroy the first contrast agent in the ROI by controlling a probe to transmit the flash pulse from transducer elements corresponding to the ROI from among a plurality of transducer elements of the probe.

3. The ultrasound diagnosis apparatus of claim 1, wherein the controller is further configured to transmit the flash pulse to destroy the first contrast agent in the ROI by determining the ROI as a focusing region and performing beamforming based on the determined focusing region.

4. The ultrasound diagnosis apparatus of claim 1, wherein the controller is further configured to receive a user input that adjusts a mechanical index of the flash pulse and transmit the flash pulse having the adjusted mechanical index.

5. The ultrasound diagnosis apparatus of claim 1, wherein the controller is further configured to control the display to display an image indicating the ROI in the ultrasound image at a position of the ROI in the contrast image.

6. The ultrasound diagnosis apparatus of claim 1, further comprising a user input interface configured to receive a user input for setting the ROI in the at least one of the ultrasound image and the contrast image of the object.

7. The ultrasound diagnosis apparatus of claim 1, wherein the controller is further configured to, in response to a user input that measures a certain region in the ultrasound image being received, determine the measured certain region as the ROI.

8. The ultrasound diagnosis apparatus of claim 1, wherein the ultrasound image is a color Doppler image, and
   the controller is further configured to determine a region where a color Doppler flow in the color Doppler image is displayed as the ROI.

9. The ultrasound diagnosis apparatus of claim 1, wherein the controller is further configured to control the display to display the ultrasound image and the contrast image together and display a position of a region in the ultrasound image corresponding to the ROI set in the contrast image, on the ultrasound image.

10. The ultrasound diagnosis apparatus of claim 1, wherein the controller is further configured to, based on the ROI being determined, display an expected contrast image to be obtained when the flash pulse is transmitted to the determined ROI.

11. A method of obtaining a contrast image, the method comprising:
    obtaining an ultrasound image and a contrast image of a scan region of an object, wherein the contrast image is an image showing a signal reflected by an injected contrast agent;
    determining a region of interest (ROI) in at least one of the ultrasound image and the contrast image, wherein the contrast agent includes a first contrast agent in the ROI and a second contrast agent in an area other than the ROI;
    transmitting a flash pulse to destroy the first contrast agent; and
    displaying a flow image of the second contrast agent re-introduced into the ROI by imaging the second contrast agent re-introduced into the ROI,
    wherein displaying the flow image includes: when a tumor is in the ROI, displaying the flow image showing a flow of the second contrast agent flowing into the tumor as the second contrast agent is re-introduced into the ROI.

12. The method of claim 11, wherein the transmitting of the flash pulse to destroy the first contrast agent in the ROI comprises controlling a probe to transmit the flash pulse from transducer elements corresponding to the ROI from among a plurality of transducer elements of the probe.

13. The method of claim 11, wherein the transmitting of the flash pulse to destroy the first contrast agent in the ROI comprises determining the ROI as a focusing region and performing beamforming based on the determined focusing region.

14. The method of claim 11, further comprising receiving a user input that adjusts a mechanical index of the flash pulse and transmitting the flash pulse having the adjusted mechanical index.

15. The method of claim 11, further comprising, based on the ROI being determined in the at least one of the ultrasound image and the contrast image, displaying an image indicating the ROI in the ultrasound image at a position of the ROI in the contrast image.

16. The method of claim 11, wherein the determining of the ROI in the at least one of the ultrasound image and the contrast image comprises receiving a user input for setting the ROI in at least one of the ultrasound image and the contrast image.

17. The method of claim 11, wherein the determining of the ROI in the at least one of the ultrasound image and the contrast image comprises, in response to a user input that measures a certain region in the ultrasound image being received, determining the measured certain region as the ROI.

18. The method of claim 11, wherein the ultrasound image is a color Doppler image, and
  the determining of the ROI in the at least one of the ultrasound image and the contrast image comprises determining a region where a color Doppler flow in the color Doppler image is displayed as the ROI.

19. The method of claim 11, further comprising, based on the ROI being determined in the at least one of the ultrasound image and the contrast image, displaying the ultrasound image and the contrast image together and displaying a position of a region in the ultrasound image corresponding to the ROI set in the contrast image, on the ultrasound image.

20. The method of claim 11, further comprising, based on the ROI being determined, displaying an expected contrast image to be obtained when the flash pulse is transmitted to the determined ROI.

* * * * *